United States Patent [19]
Alther

[11] Patent Number: 6,165,485
[45] Date of Patent: Dec. 26, 2000

[54] BIOCIDAL ORGANOCLAY

[75] Inventor: George Alther, Ferndale, Mich.

[73] Assignee: Biomin, Inc., Ferndale, Mich.

[21] Appl. No.: 09/123,680

[22] Filed: Jul. 28, 1998

[51] Int. Cl.[7] .................................................. A01N 25/12
[52] U.S. Cl. .................. 424/421; 424/405; 424/409; 424/667; 424/668; 424/669; 423/700; 502/60
[58] Field of Search ........................ 424/405, 409, 424/421, 667–672, 682, 724; 423/700–708; 502/60, 62, 80, 85, 86; 514/556, 769, 770, 949

[56] References Cited

U.S. PATENT DOCUMENTS

| | | | |
|---|---|---|---|
| 4,402,881 | 9/1983 | Alther | 260/448 |
| 4,522,800 | 6/1985 | Baltes et al. | 423/329 |
| 4,737,353 | 4/1988 | Flanigen et al. | 423/306 |

OTHER PUBLICATIONS

Abstract HCAPLUS Dn 67:36683 Mukherjee et al J. Indian Chem. Soc. 44(3)167–74, 1967.
Abstract HCAPLUS DN 127: 267320 Tsuru JPN Kokai JP 09239012, Sep. 1997.
HACAPLUS Abstract DN 114: 110461 Bors, J. Radio Chem. Acta. 51(3) 139–143, 1990.

*Primary Examiner*—Neil S. Levy
*Attorney, Agent, or Firm*—Young & Basile P.C.

[57] ABSTRACT

A bentonite based organoclay, when mixed with a biocidal quaternary amine containing a benzyl molecule within its structure, acts as a reasonably effective biocide.

When this organoclay is further treated with iodine and iodide compounds, its efficiency is greatly enhanced.

11 Claims, No Drawings

BIOCIDAL ORGANOCLAY

FIELD, BACKGROUND AND PRIOR ART OF THE INVENTION

Quaternary ammonium compounds have been widely used as bactericides, algicides and molluscicides to treat circulating or static bodies of water. These compounds are used in the water treatment of cooling towers, pool, and spa industries. The traditional quaternary amine compounds are of the higher alkyl and dialkyl variety.

Some of their disadvantages are limited spectrum of biocidal activity, high foaming characteristics, inherent toxicity, disagreeable odor production, and inhibited use in hard water. U.S. Pat. Nos. 4,444,790; 4,450,174; 5,015,395 reveal some of the background. U.S. Pat. No. 5,290,805 describes the use of decyl (nonyl)-and decyl/isononyl dimethyl ammonium chloride compounds which do not have these problems. Other quaternary amines that have been used as biocides are: didecyl dimethyl ammonium chloride (trade name Bardac 2250, Lonza); N-alkyl (C14-50%; C12-40%; C16-10%) dimethyl benzyl ammonium chloride (Barquat MB50, Lonza); Diisodecyl dimethyl ammonium chloride (BTC 99, Stepan); poly (oxyethylene ((dimethylimino)) ethylenedimethyl imino ethylene dichloride; Buckman WSCP). N-Alkyl (C14, 95%; C12, 3%; C16-2%) dimethyl benzyl ammonium chloride (Bio-Quat 50-28, Bio-Lab).

The amount of quaternary compounds that are used in water depend on the particular application. In pools, spas and other stationary bodies of water, the amount of quaternary amine dissolved in water is broadly between about 0.5 and 10 ppm. In circulating bodies of water such as recirculating cooling towers, air washers, and once through cooling systems, the concentration of quaternaries is as high as 100 ppm. The pH of the water should be between 4 and 10.

Oswald, in U.S. Pat. No. 4,188,380, describes organically modified clays where the modifier is a higher dialkyl phosphonium salt, which has biocidal properties. Another U.S. Pat. No. 4,929,644, describes blending a standard organoclay modified with di-methyl di-hydrogenated tallow ammonium chloride with another organoclay modified with a biocidal quaternary amine of the type di-methyl di-hydrogenated tallow benzyl ammonium chloride. The first organoclay imparts thickening properties to cosmetic compounds, while the second one adds biocidal activity. Neither patent suggests modifying the quaternary amine itself while preparing the organoclay.

Another type of bactericide or biocide are iodine impregnated resins. The iodine/resin disinfectant may be used to sterilize a fluid such as water or air. The disinfectant is used to devitalize microorganisms such as bacteria and viruses, which may be present in the fluid (e.g. water, air, pus, and the like). U.S. Pat. No. 5,639,452 and numerous others teach iodine/resin disinfectants obtained by contacting a strong base anion exchange resin with a suitable source of tri-iodide ions.

The terms "tri-iodide", "tri-iodide ions" and the like, as used in the context herein, refer to or characterize a substance or a complex containing three iodine atoms and which has a valence of −1. The tri-iodide ion herein therefore is a complex ion which may be considered as comprising molecular iodine (i.e. iodine as $I_2$) and an iodine ion (i.e. I—). Similarly, the terms "poly-iodide", "poly-iodide ions" and the like, refer to or characterize a substance or a complex as having three or more iodine atoms and which may be formed if more of the molecular iodine combines with the mono-valent tri-iodide ion. These terms are more particularly described in the above referred U.S. Patents. U.S. Pat. No. 5,639,452 teaches a process comprising contacting a porous strong base ion exchange resin in a salt form other than the iodide form I— with a sufficient amount of an iodine substance absorbable by the anion exchange resin such that the anion exchange resin absorbs said iodine-substance so as to convert the anion exchange resin to the disinfectant-resin, said iodine substance being selected from the group comprising poly-iodide ions having a valence of −1, being absorbed by the anion exchange resin. This process takes place through several conversion steps at 100 degrees C., up to 210 degrees C., and elevated pressure up to 100 psig.

The anion exchange resin may be in the hydroxyl form OH— or chloride form Cl—, and is contacted with a composition comprising a mixture of KI, $I_2$ and a minor amount of water, the mole ratio of KI to $I_2$ initially being about 1.

Anion exchange resins are very expensive. Given the elaborate conversion process required to create iodinated resins, the price per pound is so high as to price the product out of industrial markets.

It has been found that no patents exist for the manufacture of such disinfectants using substrates other than resins. Prior art in the manufacture of organically modified clays (from hereon called organoclays) shows that quaternary amines with biocidal properties have been in use for many years. However, applicant found it possible to combine organoclays with biocidal quaternary amines and iodine compounds, to manufacture granules of such clays and to place them into a cartridge. When water with bacteria was passed through the cartridge, essentially all bacteria were killed.

SUMMARY OF THE INVENTION

A bentonite is first modified with a biocidal quaternary amine, followed by iodination of the mix. This results in a strongly biocidal organically modified clay similar to iodinated anion exchange resins. Test results showed that when an organically modified clay is modified with a biocidal quaternary amine and then iodinated, the result is a more potent biocide than with a biocidal quaternary amine alone.

DETAILED DESCRIPTION OF THE INVENTION

A biocidal organoclay was prepared by combining a bentonite with a quaternary amine. This was done simply by blending a pre-measured amount of bentonite with quaternary amine in the amount of 10–90 percent of the bentonite's dry weight, in a container, the quaternary amine having biocidal properties, such as alkyl dimethyl benzyl ammonium chloride, a commercial disinfectant from Lonza. Other biocidal quaternary ammonium compounds are mentioned in the background description. Within the context of this disclosure, organically modified clays and zeolites will be referred to as "organominerals" or "organically modified minerals." The ratio of quaternary amine to bentonite can be varied from 5 gram amine to 100 gram of bentonite to 130 gram amine or higher. These processes are well known to those skilled in the art of organoclay manufacture. After drying, the organoclay was ground to yield a particle diameter of between 1 to 2 mm. Fines were then decanted and the clay was washed four times with sterile de-ionized water. Fines were decanted after each wash.

The clay was poured into a 13×2.5 cm column with a bed volume of 50 ml. The column was washed with 125 ml of sterile de-ionized water and then attached to a reservoir of de-chlorinated tap water inoculated with E. coli. Water in the reservoir was stirred throughout the procedure to provide a homogenous suspension of bacteria. The initial flow rate was adjusted to 2.5 ml/min yielding a residence time of 10 minutes. All samples were asceptically collected and analyzed for bacteria as described below. Samples were collected from both the reservoir of supply water to the column and from the column effluent after the passage of two column volumes, ten column volumes and 100 column volumes through the organoclay. Following the final sample collection, the column was stored for possible use at a later time.

Another biocidal clay was prepared by using the same type of quaternary amine, but it was double treated by adding equal quantities of crystalline iodine and potassium iodide to the slurry, which had previously been dissolved in a small amount of water. For example, 50 millequivalent of each chemical might be dissolved in 5 milliliters of water. This solution is then added to the bentonite-amine mix, strongly mixed in a mechanical mixer, and let stand overnight. The product takes on a brown to black color. This method yields a tri-iodide organoclay.

DESCRIPTION OF BACTERIAL CULTURING AND ENUMERATION

Bacterial Culturing and Enumeration. E. coli was cultured in a nutrient broth, then added to the dechlorinated tap water at a concentration of approximately 10 CFU/ml. CFU= colony forming units. The E. coli were enumerated by both spread plate counts using standard microbiological methods and by fluorescent microscopy of acridine orange stained bacteria. An aliquot of each sample was serially diluted and plated in duplicate onto tryptic soy agar plates for enumeration of viable bacteria after incubation at 35 degrees C. for 14–20 hours. Another aliquot of each sample was added to a glutaraldehyde fixative, stained with acridine orange, and live and dead bacteria were counted by fluorescent microscopy by averaging counts of 20 random fields viewed under oil with a magnification of 1000 times.

RESULTS

EXAMPLE 1

Physical/Chemical Properties of Industrial Wastewater.

The temperature, dissolved oxygen and pH of the wastewater were determined using conventional methods.

TABLE I

| Wastewater Properties | |
|---|---|
| Temperature | 20.1° C. |
| Dissolved oxygen | 0.3 mg/l |
| pH | 8.436 |

Wastewater Treatment and Bacterial Enumeration.

Total heterotrophs were enumerated by the standard spread plate method. Serial dilutions were prepared for enumeration from the hydrated organoclay, organoclay rinses, the wastewater sample, column flowthrough, and column washes as shown in Table II.

TABLE II

| | Bacterial Enumeration | | |
|---|---|---|---|
| Sample Standard Organoclay | CFU/ml | Volume | Total CFU |
| wastewater | $1.8 \times 10^6$ | 50 ml | $9.0 \times 10^7$ |
| resin hydrating water | 0 | 150 ml | 0 |
| prewash | 0 | 250 ml | 0 |
| Total CFU applied to column | | | $9.0 \times 10^7$ |

TABLE II-continued

| | Bacterial Enumeration | | |
|---|---|---|---|
| Sample Standard Organoclay | CFU/ml | Volume | Total CFU |
| effluent | $2.5 \times 10^6$ | 50 ml | $1.3 \times 10^8$ |
| wash #1 | $4.0 \times 10^5$ | 50 ml | $2.0 \times 10^7$ |
| wash #2 | $1.5 \times 10^5$ | 50 ml | $7.5 \times 10^6$ |
| wash #3 | $1.2 \times 10^5$ | 50 ml | $6.0 \times 10^6$ |
| Total CFU in effluent | | | $1.6 \times 10^8$ |

CFU=Colony Forming Units. Methods: The standard organoclay was passed through a 2 mm sieve. The retentate was then collected from a 1 mm sieve and used for the preparation of the column. Thus, the column was prepared using 1 to 2 mm diameter particles. The clay was hydrated for one hour in sterile deionized water. Fines were decanted after each wash and the clay was washed 4 times with 150 ml of sterile deionized water. Fines were decanted after each wash. The organoclay granules were packed in a 13×2.5 cm. column with a bed volume of 50 ml. The column was washed 5 times with 50 ml of water, and then was allowed to drain. Wastewater was applied to the column and allowed to sit for ten minutes before starting the flow at a rate of 1.7 ml/min. The column was then washed three times with 50 ml sterile deionized water. All effluent was asceptically collected. All fractions were serially diluted and plated in duplicate onto R2A agar plates for bacterial enumeration.

This test showed that a standard organoclay does not cause killing of bacteria, even after 10 minutes of exposure.

EXAMPLE 2

The organoclay in this study was treated with a biocidal quatemary amine, meaning an amine that includes a benzene molecule, such as alkyl dimethyl benzyl ammonium chloride.

Physical/Chemical Properties of Industrial Wastewater.

The temperature, dissolved oxygen and pH of the wastewater were determined using conventional methods and shown in Table III.

TABLE III

| Wastewater Properties | |
|---|---|
| Temperature | 20.7° C. |
| Dissolved oxygen | 0.1 mg/ml |
| pH | 7.14 |

WASTEWATER TREATMENT and BACTERIAL ENUMERATION.

Total heterotrophs were enumerated by spread plate counts using standard microbiological methods. Bacteria were enumerated from the hydrated resin, resin rinses, the wastewater sample, column flow through, and column washes.

TABLE IV

| | Bacterial Enumeration | | |
|---|---|---|---|
| sample | CFU/ml | Volume | Total CFU |
| wastewater | $6.1 \times 10^7$ | 50 ml | $3.0 \times 10^9$ |
| resin hydrating water | 0 | 100 ml | 0 |
| rinse #1 | 0 | 200 ml | 0 |
| rinse #2 | 0 | 150 ml | 0 |

TABLE IV-continued

Bacterial Enumeration

| sample | CFU/ml | Volume | Total CFU |
|---|---|---|---|
| rinse #3 | 0 | 175 ml | 0 |
| Total CFU introduced to resin | | | $3.0 \times 10^9$ |
| effluent | $2.8 \times 10^5$ | 50 ml | $1.4 \times 10^7$ |
| wash #1 | $3.2 \times 10^3$ | 50 ml | $1.6 \times 10^5$ |
| wash #2 | 0 | 50 ml | 0 |
| wash #3 | 0 | 250 ml | 0 |
| Total CFU after treatment | | | $1.4 \times 10^2$ |

CFU=Colony Forming Units. Methods: The iodide treated organoclay resin was soaked overnight in sterile deionized water. Fines were then decanted, and the resin was packed in a 13×2.5 cm. column. The bed volume was 50 ml. The hydrating water was collected along with the water from subsequent rinses of the prepared column. The column was allowed to drain after the third rinse. Wastewater was then applied to the column and allowed to sit for five minutes before starting a flow through the column. The flow was adjusted to approximately 1 ml/minute and effluent was collected into a sterile collection tube while the column drained. The column was then washed three times with sterile deionized water and the wash was collected as the column drained. All fractions were then serially diluted and plated onto dupliate R2A agar to enumerate bacteria.

Discussion

Results of this laboratory study on the efficacy of the benzyl amine treated organoclay for removing bacteria from industrial wastewater demonstrated that a major percentage (99.5%) of the bacteria are removed with a single pass through a column prepared with the resin. In particular, the number of bacteria in the wastewater decreased from $6.1 \times 10^7$ CFU/ml before treatment to $2.8 \times 10^5$ CFU/ml after being exposed to the resin for at least five minutes. This loss is attributable to the bactericidal properties of the clay-iodide composite.

EXAMPLE 3

This example shows the results of an iodinated organoclay where the grain size was U.S. mesh 8×30, as shown in Table V.

This sample was prepared by hand mixing the bentonite with the quaternary amine in a container, and then adding the iodine compounds. The mix was then passed through a laboratory meatgrinder to ensure thoughrough mixing.

Discussion

The sample of double-treated 8×30 mesh organoclay used in this study was greater than 99.999% effective in killing *E. coli* inoculated into tap water at a concentration of $10^5$ CFU/ml. Fluorescent microscopy indicated that initially about 40% of the bacteria applied to the column were not observed coming off the column. These bacteria were either lysed during passage over the clay or they were adsorbed onto the clay or column surface. Results of the spread plating show that >99.999% bacteria which did pass through the column were dead. After passage of 100 column volumes almost all of the bacteria applied to the column were passing through the material (94%). However, >99.999% of these bacteria were dead as well as shown by spread plating. The sterilization capacity of the organoclay is expressed as the volume of treated water per volume of satured resin at which the killing efficacy is still >99.999%. Results of this laboratory study demonstrated that the sterilization capacity of the doubly-treated organo-clay of the present invention is at least one hundred times the volume of the satured resin.

EXAMPLE 4

In this test the grain size of the iodinated organoclay with the biocidal quatemary amine is reduced to U.S. mesh 16×30, with the following results. This was done by crushing the grains to a finer size and passing them through two screens of 16 and 30 U.S. mesh size.

Physical/Chemical properties of Industrial Wastewater.

The temperature, dissolved oxygen and pH of the wastewater were determined using conventional methods as shown in Table VI.

TABLE VI

| Wastewater Properties | |
|---|---|
| Temperature | 23.3° C. |
| Dissolved oxygen | 0.1 mg/ml |
| pH | 7.24 |

Wastewater Treatment and Bacterial Enumeration. Total heterotrophs were enumerated by spread plate counts using standard microbiological methods. Bacteria were enumerated from the hydrated resin, resin rinses, the wastewater sample, column flow through, and column washes as shown in Table VII.

TABLE V

Bacterial Enumeration

| | Supply Water | | Column Effluent | | % Loss after Exposure to Organo-Clay | |
|---|---|---|---|---|---|---|
| # of Column Volumes | Ave. # of Stained Bacteria/Field | CFU/ml | Ave. # of Stained Bacteria/Field | CFU/ml | % Stained Bacteria | % Killed Bacteria |
| 2 | 9.7 | $1.2 \times 10^5$ | 5.9 | 0 | 39% | >99.999% |
| 10 | 8.4 | $1.6 \times 10^5$ | 5.0 | 0 | 40% | >99.999% |
| 100 | 19.8 | $2.2 \times 10^5$ | 18.6 | 0 | 6% | >99.999% |

TABLE VII

Bacterial Enumeration

| Sample | CFU/ml | Volume | Total CFU |
|---|---|---|---|
| wastewater | $3.1 \times 10^5$ | 50 ml | $1.5 \times 10^7$ |
| resin hydrating water | 0 | 150 ml | 0 |
| rinse | 0 | 250 ml | 0 |
| Total CFU introduced to resin | | | $1.5 \times 10^7$ |
| effluent | 0 | 50 ml | 0 |
| wash #1 | 0 | 50 ml | 0 |
| wash #2 | 0 | 50 ml | 0 |
| wash #3 | 0 | 50 ml | 0 |
| Total CFU after treatment | | | 0 |

CFU=Colony Forming Units. Methods: The clay-iodide-quaternary amine resin was forced through a 2 mm sieve. The retains were then collected from a 1 mm sieve and used for the preparation of the column. Thus, the column was prepared using 1 to 2 mm diameter resin particles. The resin was then soaked overnight in sterile dionized water. Fines were then decanted and the resin was washed 4 times with 125 ml of sterile deionized water. Fines were decanted after each wash. The resin was packed in a 13×2.5 cm column. The bed volume was 50 ml. The hydrating water was collected along with the water from a subsequent column rinse. The column was allowed to drain after the rinsing step and wastewater was applied to the column and allowed to sit for ten minutes before starting a flow at a rate of 1 ml/min. The effluent was collected in a sterile tube as the column drained. The column was then washed three times with sterile deionized water and the wash was collected as the column drained. All fractions were serially diluted and plated onto duplicate R2A agar to enumerate bacteria.

Discussion

Results of this laboratory study on the efficacy of the clay-iodide-amine organoclay for removing bacteria from industrial wastewater demonstrated that all of the bacteria are removed with a single pass though a column prepared with the organoclay. In particular, the number of bacteria in the wastewater decreased from $3.1 \times 10^5$ CFU/ml before treatment to 0 CFU/ml after being exposed to the organoclay for at least five minutes.

While the foregoing examples employed clay and bentonite based materials, similar results will be achieved utilizing organically modified zeolites. The foregoing examples are meant to illustrate some embodiments of the present invention, but are not meant to be limitations thereon. Obviously many modifications and variations of the invention are possible in light of the above teachings. Therefore it is to be understood that within the appended claims, the invention may be practiced otherwise than specifically described.

What is claimed is:

1. A modified organic bactericidal mineral media, said media comprising:
   a mineral selected from the group consisting of clays and zeolites; and
   an organic modifier selected from the group consisting of a quaternary ionic compound in combination with iodine or an iodine compound, or combinations thereof, wherein said organic modifier is present in an amount sufficient to achieve a reduction in bacteria present in aqueous media contacted by the mineral media for an interval of at least five minutes, the amount of bacteria present after five minute exposure being essentially zero.

2. A modified organic media as in claim 1, wherein said mineral comprises bentonite clay.

3. A modified organic media as in claim 1, wherein said mineral is an organically modified clay selected from the group consisting of bentonite, nontronite, beidellite, stevensite, hectorite, attapulgite, saponolite, sepiolite, paligorskite, vermiculite, halloysite, kaolinite, and combinations thereof.

4. A modified organic media as in claim 1, wherein said organic material comprises a zeolite.

5. A modified organic bactericidal mineral media, said media comprising:
   a mineral selected from the group consisting of clays and zeolites; and
   an organic modifier selected from the group consisting of a quaternary ionic compound in combination with iodine or an iodine compound, or combinations thereof, wherein said organic modifier is present in an amount sufficient to achieve a reduction in bacteria present in aqueous media contacted by the mineral media for an interval of five minutes, the amount of bacteria present after five minute exposure being essentially zero.

6. A modified organic media as in claim 1, wherein said mineral comprises bentonite modified with a quaternary ammonium compound.

7. A modified organic media as in claim 1, wherein said quaternary ammonium compound comprises a benzyl quaternary ammonium compound.

8. A modified organic media as in claim 1, wherein said mineral comprises bentonite modified with a quaternary ammonium compound and is iodinated.

9. A modified organic bactericidal mineral media, said media comprising:
   a mineral selected from the group consisting of clays and zeolites; and
   an organic modifier selected from the group consisting of a quaternary ionic compound in combination with iodine or an iodine compound, or combinations thereof, wherein said organic modifier is present in an amount equal to a stoichiometric excess, and wherein said modifier is a phosphonium compounds;
   wherein said media is capable of removing and destroying at least a portion of bacterial material present in an aqueous media brought in contact with the modified organic bactericidal media.

10. A modified organic media as in claim 1, wherein said mineral is modified with a stoichiometric excess of a pyridinium compound.

11. A modified organic bactericidal mineral media, said media comprising:
    a mineral selected from the group consisting of clays and zeolites; and
    an organic modifier selected from the group consisting of a quaternary ionic compound in combination with iodine or an iodine compound, or combinations thereof, wherein said organic modifier is present in an amount equal to a stoichiometric excess, wherein said iodine compound comprises polyiodide ions;
    wherein said media is capable of removing and destroying at least a portion of bacterial material present in an aqueous media brought in contact with the modified organic bactericidal media.

* * * * *